(12) United States Patent
Thome et al.

(10) Patent No.: US 9,220,582 B2
(45) Date of Patent: Dec. 29, 2015

(54) PACKAGING SYSTEM FOR STORING, CAPTURING AND TRANSPORTING DENTAL IMPLANTS

(71) Applicant: JJGC INDUSTRIA E COMERCIO DE MATERIAIS DENTARIOS S.A., Curitiba (BR)

(72) Inventors: Geninho Thome, Curitiba (BR); Alexsander Luiz Golin, Curitiba (BR); Ilderaldo Jose Lucca, Curitiba (BR); Ivanio Pereira da Silva, Curitiba (BR); Milton Roberto Souza, Curitiba (BR)

(73) Assignee: JJGC INDÚSTRIA E COMÉRCIO DE MATERIAIS DENTÁRIOS S.A., Curitiba, PR (BR)

( * ) Notice: Subject to any disclaimer, the term of this patent is extended or adjusted under 35 U.S.C. 154(b) by 109 days.

(21) Appl. No.: 14/161,318

(22) Filed: Jan. 22, 2014

(65) Prior Publication Data

US 2014/0202892 A1    Jul. 24, 2014

(30) Foreign Application Priority Data

Jan. 23, 2013 (BR) .......................... 102013001690-0

(51) Int. Cl.
*A61B 19/02* (2006.01)
*A61C 8/00* (2006.01)

(52) U.S. Cl.
CPC ........... *A61C 8/0087* (2013.01); *A61C 2202/00* (2013.01)

(58) Field of Classification Search
CPC .... A61C 19/02; A61C 8/0087; A61C 8/0089; A61C 2202/00
USPC .......... 206/63.5, 438, 339, 368, 83, 804, 815; 433/77, 79, 97, 141, 146, 167, 229, 49, 433/172–176, 201.1
See application file for complete search history.

(56) References Cited

U.S. PATENT DOCUMENTS

| | | | |
|---|---|---|---|
| 6,217,332 B1 * | 4/2001 | Kumar | 433/173 |
| 2003/0181849 A1 * | 9/2003 | Castellanos | 604/29 |
| 2004/0112781 A1 * | 6/2004 | Hofverberg et al. | 206/438 |
| 2011/0017622 A1 * | 1/2011 | Guenter et al. | 206/368 |
| 2011/0056851 A1 * | 3/2011 | Schlottig et al. | 206/63.5 |

FOREIGN PATENT DOCUMENTS

| | | |
|---|---|---|
| BR | MU8600477 | 11/2007 |
| BR | PI0515330 | 11/2007 |
| BR | PI0902546 | 5/2011 |
| WO | 2011101167 | 8/2011 |

* cited by examiner

*Primary Examiner* — Luan K Bui
*Assistant Examiner* — Rafael Ortiz
(74) *Attorney, Agent, or Firm* — Banner & Witcoff, Ltd.

(57) ABSTRACT

Packaging system for dental implants allowing the conditioning of different types of implants due to its height regulation capacity that, additionally, eases the handling and the removal of the packaging implant by a gripper-shape mechanism, reducing damages or contamination risks of the implant before the usage.

5 Claims, 4 Drawing Sheets

PACKAGING SYSTEM FOR STORING, CAPTURING AND TRANSPORTING DENTAL IMPLANTS

RELATED APPLICATION

This application claims priority under 35 U.S.C. §119 to Brazilian patent application BR 102013001690-0, filed Jan. 23, 2013, the disclosure of which is incorporated herein by reference.

FIELD OF THE INVENTION

The present invention relates to a field of dental devices, more specifically to the conditioning and handling systems of components and dental implants, more exactly to a packaging for conditioning, capturing and transporting dental implants.

BACKGROUND

Dental implants are, as a rule, metal screws, preferably made of titanium, which act as artificial tooth roots. They are positioned in the maxillary and mandibular bones by means of surgical procedures. The implants provide a stable support for the installation of artificial teeth, called denture calls. Notably, these artifacts are manufactured in resistant alloy and with low expectation of rejection or reaction with the body and, therefore, the use of titanium became widespread.

Still, due to interaction with living tissue, the implants for single use must be sterile to minimize the risk of contamination. Each implant should be packed clean in a packaging that protects it from mechanical damage, ensure the sterility maintenance, sealing and has the objective of protecting the end user. Thus, the packaging for the said implant should be designed to preserve it from damage during the handling, transportation and storage.

One way of ensuring the safety in the procedures for installation of dental implants is by capturing and transporting the implant to the surgical alveolus. It must ensure that during the capture, the dental implant is not damaged and that, at the time of transport, the packaging allows the removal of dental implant without any retention or obstruction. So, how is known, it is always recommended, in dentistry, as well as in healthcare as a whole, the use of products equipped with full sterilization, disinfection, and also all methods to prevent surgical contamination. It is known that the product sterility is only guaranteed if healthy state of the packaging and the product, which must be secured until the time of opening.

Today, the packaging for dental implants available in the market are designed specifically for each particular type of implant, making difficult the conditioning of multiple types of implant due to dimensional issues or implant fitting in packaging. Moreover, after opening the lid, the manipulation of the implant is vulnerable to a possible fall of implant, and its consequent contamination.

With this, it is desirable an interaction between the dental implant and its packaging so that perfect accommodation of the implant is provided, minimizing the risk of damage, either by shocks due to displacement of dental implant inside the packaging or the implant accidental release for use during its capture.

However, after analyzing the existing packaging for dental implants that rely on insertion system, it was found that there are problems in its configuration that contradict the current technique of inserting the implant, which may cause a failure in surgical operation if no hard standards are adopted to appropriate security. For example, if the dental implant is not fully stable at the time of capture, it can harm the surgical procedure by its displacement. In another commonplace example, the implant can come away from the packaging and be thrown out of the surgical field, infecting and making its use unfeasible.

Still in the art, the protection MU8600477 show a packaging that eliminates the need for a specific tool, known as "assembler", composing of a seal lid that accommodates the implant internally, which fits in a fitting on an internal disk to promote the fixation of the implant. However, it does not show the same accommodation and adaptation solution to different implants foreseen in the present proposed innovation.

The document PI0515330 presents a packaging for dental implant provided from a receptacle for the implant that keep fixed until the removal for use. However, it does not show the same accommodation and adaptation solution to different implants foreseen in the present proposed innovation.

The patent application PI0902546 exposes the cylinder-shape packaging where two inner containers accommodate both the implant and the implant lid, being hermetically sealed by fitting lids. However, it does not show the same accommodation and adaptation solution to different implants foreseen in the present proposed innovation.

The invention W02011101167 elucidates one packaging of an implant in which a protective material is applied directly to the surface of the implant, forming a graft around the implant, so that such protection may be composed of polyethylene glycol hydrogels, gels consisting of derivatives of polyethylene glycol, fibrin gels, protein gels, oligomers gels, hydrocolloid gels, gelatins and mixtures thereof.

Based on the foregoing, it is understood that there are still unsolved problems in the art. Based on this fact and thinking in continuous product development, we propose an innovation, sometimes claiming the privileges of its protection for its novelty and inventive step, as explained below.

It relates to the packaging for dental implants, endowed with innovative and technological packaging system allowing the conditioning, storage, transportation and capture of any diameter and length of dental implants, which in turn reduces and facilitates the process of production and assembly of several dental implants models in a single packaging.

DESCRIPTION OF THE DRAWINGS

Exemplary embodiments of the disclosure will now be described by way of example only and with reference to the accompanying drawings, in which.

DETAILED DESCRIPTION

Figure 1:
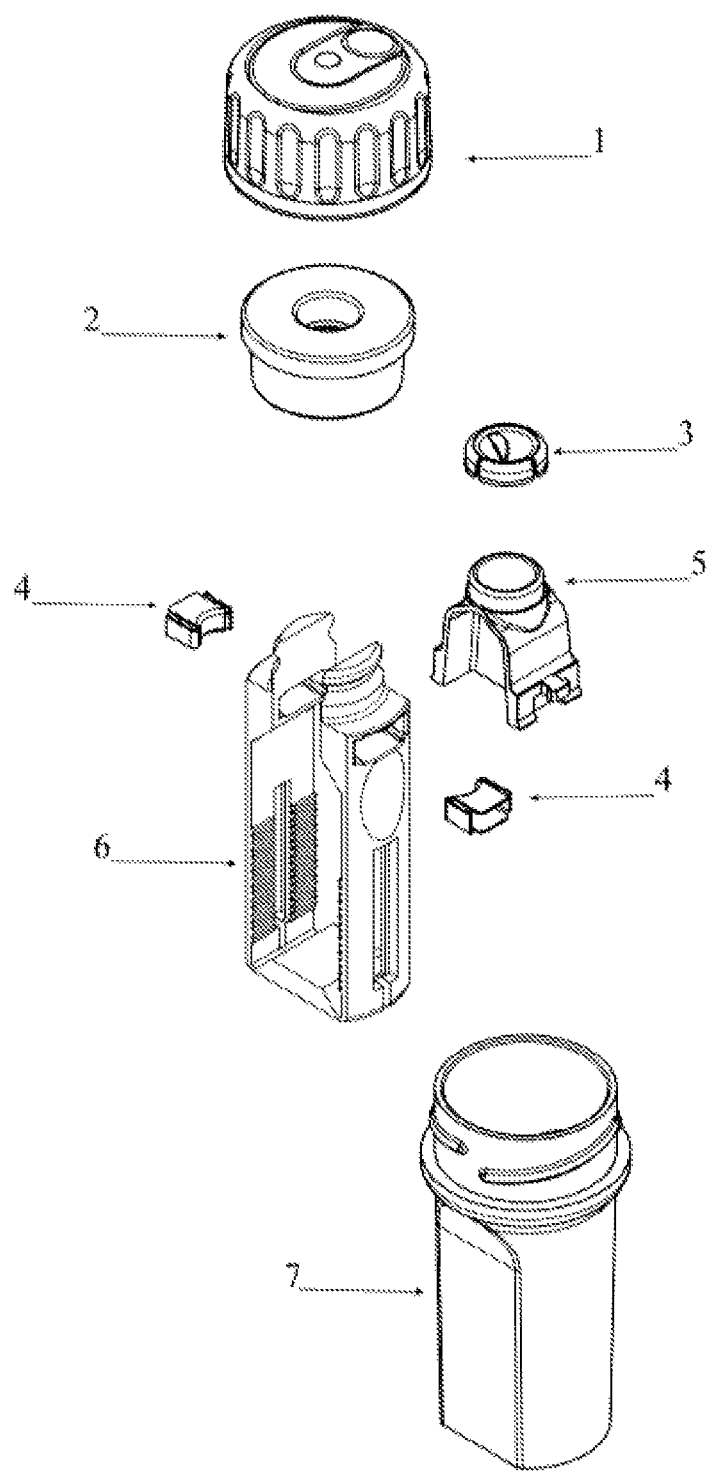
FIG. 1 illustrates an exploded view of an example of the proposed packaging, where the components can be perceived, such as the outer lid (1), the inner lid (2), the support disk of the implant apical portion (3), in titanium commercially pure, the support side grippers of the implant cervical portion (4) in titanium commercially pure, the elevator (5), the support (6) in gripper shape and the outer flask (7).
Figure 2:
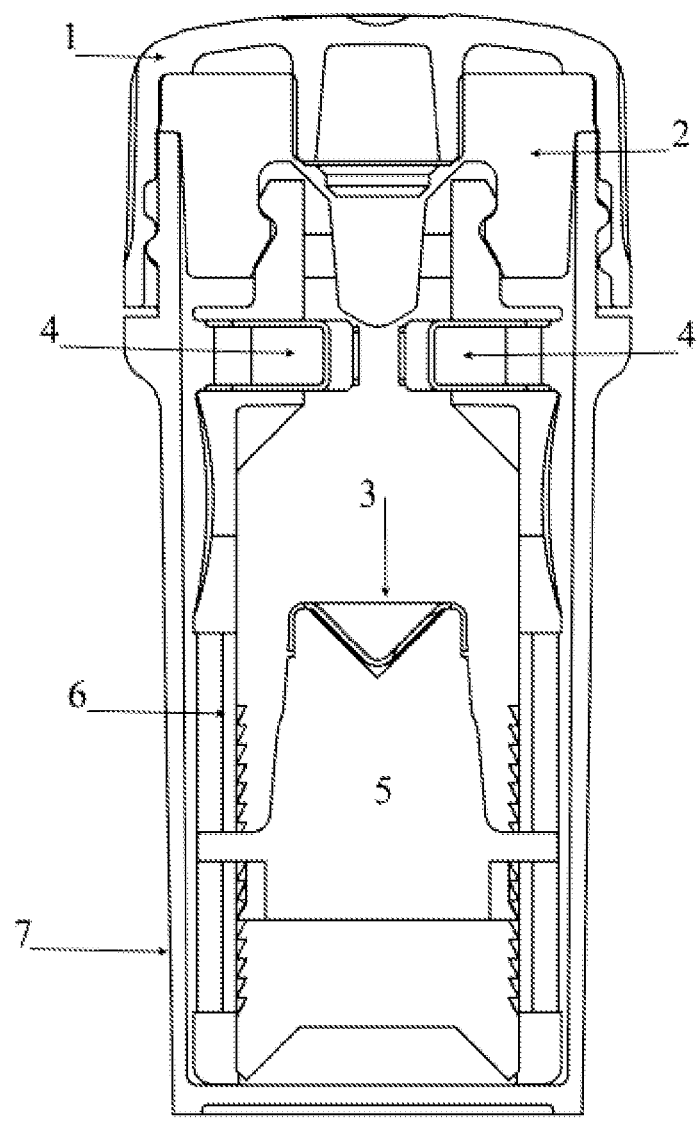
FIG. 2 illustrates a cross-section view of an example of the packaging proposed herein, where the components can be perceived when the packaging is assembled, such as the outer lid (1), the inner lid (2), the support disk of the implant apical portion (3), in titanium, the support side grippers of the implant cervical portion (4) in titanium, the elevator (5), the support (6) in gripper shape and the outer flask (7).
Figure 3:
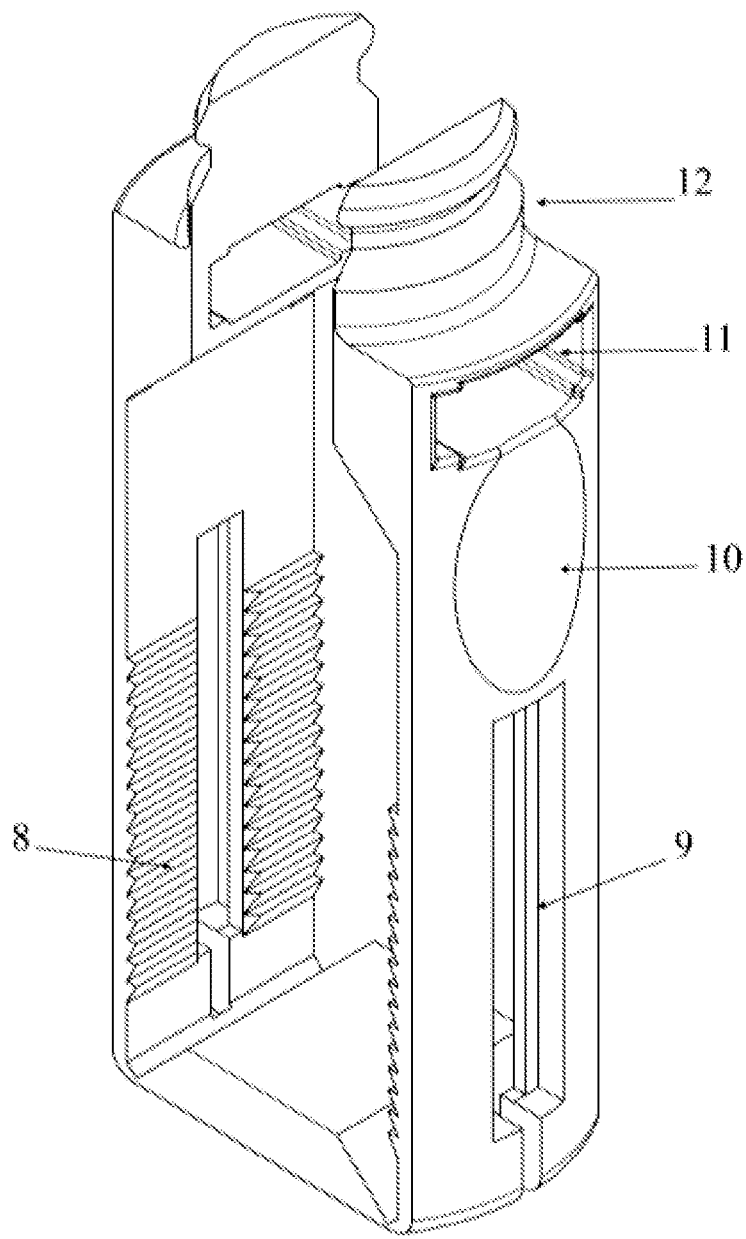
FIG. 3 illustrates in detail an example of the support (6) in gripper shape, where its mains features can be perceived, such as the side grooves (8) for elevator height regulation (5), the side slots (9) that ease the handling to manipulate the implant, the side holes (11) to insert the side grippers (4) in titanium, and the upper fittings (12) allowing the perfect support adaptation, as well as the interaction with the inner lid (2).
Figure 4:
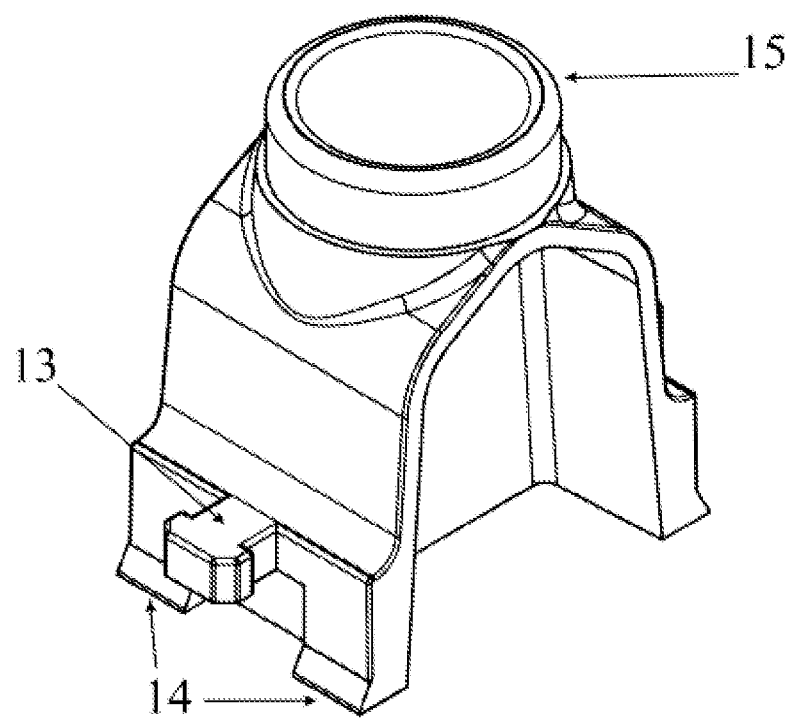
FIG. 4 illustrates in detail an example of the elevator (5), where its pyramidal conformation and its features can be perceived, such as the side coupling (13) to interact with the side slots (9) of the support (6) in gripper shape, the side protrusions (14) to interact with the side grooves (8) of the support (6) in gripper shape, and the top (15) for support disk fitting of the implant apical portion (3).

It is proposed as innovation a packaging for dental implants allowing not only the proper conditioning of the artifact, but also its capture and transport for safely implant, minimizing the risk of damage to the implant. Thus, the respective improvement was developed aiming to create a product capable of providing greater safety in use, preventing contamination and possible infection, besides possible ineffectiveness of the implant at the time of surgery.

Examples of said packaging embody a "conditioning, storing, transporting and capturing system" allowing the height labeling to accommodate different types of implants. In one example, the said system is embodied interacting the elevator (5) with the side grooves (8) of the support (6) in gripper shape. The lower part of the elevator (5) has side protrusions (14) supporting in the side grooves (8) of the support (6) in gripper shape in the desired place, allowing different regulations of the elevator height (5) inside the packaging. Side couplings (13) in the elevator body (5) interact with the side slots (9) of the support (6) in gripper shape, allowing the elevator (5) to slide vertically inside the support (6) in gripper shape, adjusting in the desired position in function of the implant to be conditioned.

The elevator (5) still has a top (15) conformed to fit the receptacle (3) in titanium to accommodate the implant, allowing to preserve the implant from any eventual damage arising from the potential migration of chemical components of the polymer to the metal. For the same reason, sideboards (4) in titanium are allocated in the side holes (11) of the removal mechanism (6) in gripper shape for interaction with the implant.

The support (6) in gripper shape is the highlight of this innovation, since it provides the most distinct functionalities of this innovation by allowing the implant conditioning in the packaging, associated with the inner lid (2), as this keeps the implant in the desired position, pressing it against the support disk of the implant apical portion (3). The support (6) in shape gripper constitutes a single body part bent so as to adapt to the outer housing (7), by inserting this completely, forming the grippers shape that allows the implant seizure safely. Side depressions (10) indicate the pressure point of the body in the removal mechanism (6) in shape gripper for the sideboards (4) in titanium secure the implant and enable its removal from the packaging and subsequent removal by means of suitable tools, constituting then a safe and reliable method of use for professionals.

The outer lid (1) screwing up the outer housing (7) and press the inner lid (2) against the removal mechanism (6) in gripper shape, so that there is an interaction of the inner lid (2) with upper protrusions (12) of the removal mechanism (6) in gripper shape and hence stabilizing the packaging inner assembly, protecting the implant. Therefore, it is desirable that the inner lid (2) is made of polymer material soft enough to allow this interaction with upper protrusions (12) of the removal mechanism (6) in gripper shape.

In this way, the packaging designed here allows the proper conditioning of the implant in a protective container, as well as the manipulation of the said implant for use by means of a mechanism allowing the safe removal of the packaging for later use.

Also, since the packaging presented here allows the accommodation of dental implants of different diameters and lengths, facilitating and decreasing the production process and assembly of different models in a single packaging. Additionally, the reduction of the variability of packaging facilitates the storage, handling and movement of the materials, reducing the time to perform these tasks by providing a standardization of these methods, moving and storage equipment, with a consequent reduction in costs, besides the benefits to the environment, since it has a less aggressive production due to radical reduction in the volume to be transported.

Thus, this new packaging focuses, beyond the unification of models, material reduction in the production, storage and transportation savings, sterility guaranteed.

This innovation is not limited to the examples commented and illustrated herein, and should be understood in its all-encompassing scope. Many modifications, such as the number of various components or the materials used, and other examples of the innovation will come to the mind of one skilled in the art to which this innovation belongs, having the benefit of the teachings presented in the foregoing descriptions and drawings. Furthermore, it is to be understood that the innovation is not limited to the specific forms disclosed, and that modifications and other shapes are understood as included within the scope of the attached claims. Although specific terms are employed herein, they are used only in a generic and descriptive purpose and not as limiting way.

The invention claimed is:

1. A packaging system for storing, capturing and transporting a dental implant comprising:
    a removal mechanism having a gripper shape and being associated to an elevator, the elevator being configured to regulate the height of the dental implant for proper positioning of said dental implant;
        wherein the removal mechanism comprises one or more side grooves configured to regulate the height of the elevator, one or more side depressions configured to manipulate the implant, one or more side holes configured to receive one or more sideboards, one or more upper protrusions configured to fit and interact with an inner lid, and one or more side slots; and
        wherein the elevator comprises one or more side couplings configured to interact with the one or more side slots of the removal mechanism, one or more side protrusions configured to interact with the one or more side grooves of the removal mechanism, and a top configured to fit a receptacle;
    an outer housing; and
    an outer lid, wherein the outer lid is configured to enclose the removal mechanism and elevator after they are inserted into the outer housing, and wherein the outer lid is further configured to, when the removal mechanism and elevator are enclosed, press against the inner lid such that the inner lid presses against the removal mechanism for maintenance of the implant in its desired position.

2. The packaging system of claim 1, wherein the inner lid comprises an elastic polymer material.

3. The packaging system of claim 1, wherein the inner lid consists of an elastic polymer material.

4. The packaging system of claim 1, wherein the sideboards and receptacle comprise titanium.

5. The packaging system of claim 1, wherein the sideboards and receptacle consist of titanium.

\* \* \* \* \*